US006621087B1

(12) United States Patent
Bisges et al.

(10) Patent No.: US 6,621,087 B1

(45) Date of Patent: Sep. 16, 2003

(54) COLD LIGHT UV IRRADIATION DEVICE

(75) Inventors: Michael Bisges, Lippstadt (DE); Knut Kisters, Bielefeld (DE)

(73) Assignee: arccure technologies GmbH, Lippstadt (DE)

( * ) Notice: Subject to any disclaimer, the term of this patent is extended or adjusted under 35 U.S.C. 154(b) by 0 days.

(21) Appl. No.: 09/623,784

(22) PCT Filed: Feb. 26, 1999

(86) PCT No.: PCT/EP99/01244

§ 371 (c)(1),
(2), (4) Date: Sep. 8, 2000

(87) PCT Pub. No.: WO99/46546

PCT Pub. Date: Sep. 16, 1999

(30) Foreign Application Priority Data

Mar. 11, 1998 (DE) ........................................ 198 10 455

(51) Int. Cl.$^{7}$ ............................ G01J 1/00; A61N 5/00; G21G 5/00

(52) U.S. Cl. ................................ 250/492.1; 250/504 R

(58) Field of Search .......................... 250/492.1, 504 R

(56) References Cited

U.S. PATENT DOCUMENTS 3,255,342 A 6/1966 Seitz et al.
3,463,914 A 8/1969 Lutter
3,769,503 A 10/1973 Kim
4,048,490 A 9/1977 Troue
4,101,424 A 7/1978 Schooley et al.
4,143,278 A * 3/1979 Koch ......................... 250/527
4,177,383 A 12/1979 Knight
4,222,177 A 9/1980 Mason
4,563,589 A * 1/1986 Scheffer ................. 250/504 R
4,591,958 A * 5/1986 Lamboo ................. 250/504 R
4,644,899 A 2/1987 Glaus
4,798,960 A 1/1989 Keller et al.
4,839,522 A 6/1989 Bourgeois et al.
4,864,145 A 9/1989 Burgio, Jr.
4,937,714 A 6/1990 Witt
5,502,310 A 3/1996 Niestrath et al.
5,667,850 A * 9/1997 Gaven et al. ............... 427/510
5,722,761 A * 3/1998 Knight ........................ 362/96
5,751,008 A 5/1998 Jung et al.

FOREIGN PATENT DOCUMENTS

CH 415840 6/1966
DE 1497325 10/1969

(List continued on next page.)

*Primary Examiner*—Bruce Anderson
(74) *Attorney, Agent, or Firm*—Milde & Hoffberg LLP

(57) ABSTRACT

A cold light UV irradiation device is used for curing UV paint and UV printing dyes on heat-sensitive substrates (12,13). It is used, for example, in plants for printing on packaging foils or in the production line for CD□s (Compact Discs) and DVD□s (Digital Versatile Discs). The irradiation devices used until now emit in addition to the UV radiation also a high portion of heat radiation (IR Radiation) onto the substrate (12,13), which often leads to deformation and brittleness of the substrate. The present invention allows an effective separation of the UV radiation from the IR radiation. With short beam paths, a high UV intensity with a low heat load of the substrate is realized.

36 Claims, 6 Drawing Sheets

FOREIGN PATENT DOCUMENTS

| | | | |
|---|---|---|---|
| DE | 2455458 | A1 | 6/1975 |
| DE | 26 22 993 | A1 | 9/1976 |
| DE | 2726387 | A1 | 3/1978 |
| DE | 2820399 | A1 | 11/1979 |
| DE | 2830870 | A1 | 1/1980 |
| DE | 30 44 081 | A1 | 9/1981 |
| DE | 3124335 | A1 | 1/1983 |
| DE | 3529800 | A1 | 3/1986 |
| DE | 3526082 | C2 | 9/1988 |
| DE | 38 01 283 | C1 | 8/1989 |
| DE | 9014652 | U1 | 4/1992 |
| DE | 3902643 | C2 | 12/1992 |
| DE | 4301718 | A1 | 7/1994 |
| DE | 4318735 | A1 | 12/1994 |
| DE | 44 09 426 | A1 | 9/1995 |
| DE | 19516053 | A1 | 11/1996 |
| DE | 19547252 | A1 | 6/1997 |
| DE | 19651977 | A1 | 6/1998 |
| EP | 0222060 | A2 | 7/1986 |
| EP | 0339130 | A2 | 11/1988 |
| EP | 0741272 | A2 | 4/1996 |
| GB | 1482 743 | | 8/1977 |
| WO | WO 96/28302 | | 9/1996 |

* cited by examiner

COLD LIGHT UV IRRADIATION DEVICE

FIELD OF THE INVENTION

The present invention relates to a device for curing a UV coating, in particular a UV paint coating, or of UV printing dyes, on a substrate, in particular on heat-sensitive materials.

BACKGROUND OF THE INVENTION

Cold light UV irradiation devices are used in the coating of substrates of heat-sensitive materials, particularly synthetics, with UV paints and printing dyes. The substrates may be present in the shape of formed objects (bottles, discs, etc.) or as foils and strips. Disc-shaped objects may be optical information carriers such as Compact Discs (CD's) or Digital Versatile Discs (DVD's), for example. Other temperature-sensitive irradiation goods are ceramic-type materials such as those used in electronic components, for example. Metal and synthetic parts used in electronic components are often temperature-sensitive as well.

A high UV light intensity is necessary to cure the UV paint and printing dyes within the short cycle times of high-volume production lines. Usually, UV light in the wavelength range of 200 to 400 nm is used for curing. However, all common light sources also emit the long-wave heat radiation (infrared radiation/IR radiation) in addition to the UV light required for curing. However, the long-wave heat radiation leads to deformation and brittleness of the substrate and is, therefore, undesirable.

It is known from DE 39 02 643 C2 to position the light source directly above the irradiation goods and to place two cold light mirrors behind the light source to reduce the heat radiation. The disadvantage is that a great heat portion reaches the substrate from the lamp because of the direct beam path.

G 901 46 52.2 and DE 440 942 6 show arrangements that lower the heat load of the object with a heat filter in the direct beam path. These heat filters consist of a coated quartz glass disc and only slightly reduce the infrared radiation to the substrate. Furthermore, the quartz glass discs also absorb a portion of the UV radiation.

From U.S. Pat. No. 4,048,490, an arrangement is known where the direct beam path to the substrate is prohibited. The direct beam path is guided by a reflecting barrier past the lamp to reflectors located underneath the lamp and from there to the substrate. The extremely long beam paths are a disadvantage of this arrangement. The UV intensity decreases with an increasing length of the beam path. Another disadvantage is that the barrier also reflects the heat radiation entirely, resulting in an insufficient separation of the UV and the IR radiation. Furthermore, this arrangement can illuminate the substrate only two-dimensionally because the lamp and barrier constitute two radiation sources. The complex geometric arrangement of the reflectors and the required distance between the barrier and lamp require a very large assembly space for such arrangements. Thus, they cannot be used in small production lines.

Known from DE 38 01 283 C1 is a device for curing a UV protective paint coating on flat objects, where a flat output nozzle is located between the device and the object and where inert gas, for example nitrogen, is provided via a feed line to said nozzle, which replaces the oxygen of the air during the irradiation process and can lead to better quality of the cured protective paint coating.

An UV lamp arrangement for curing photo-polymerizable materials is known from DE 26 22 993 A1. To remove the heat radiation that cannot be used for curing, the lamp is surrounded by a water jacket made of clear molten quartz. One embodiment has a semi-circular reflective coating directly on the quartz sheathing of the lamp. It focuses the radiation of the lamp generally in the direction of the focussing plane in the neighborhood of the substrate.

SUMMARY AND OBJECTS OF THE INVENTION

Based on this state-of-the-art, it is the objective of the invention to create a device for curing a UV coating that enables an effective separation of the UV radiation from the IR radiation in order to reduce the heat load of the substrate and at the same time to achieve a high UV intensity through short beam paths.

In one embodiment of the invention, it is possible to focus the UV radiation on the substrate.

According to a first exemplary embodiment of the present invention, this objective is achieved by a device for curing a UV coating, in particular a UV paint coating, or of UV printing dyes, on a substrate, in particular on heat-sensitive materials, with at least one light source that is located above the substrate, where the light of said light source can be directed to the UV coating via a reflector system for purposes of curing, where at least one barrier prevents, at least partially, the direct beam path of the light source from striking the substrate, characterized in that the UV radiation emitted by the light source is reflected by a UV reflection coating of the barrier through the light source to the reflectors located behind the light source, and the barrier includes at least one heat absorbing body that absorbs, at least partially, the heat radiation emitted by the light source.

According to a second exemplary embodiment of the present invention, this objective is achieved by a device for curing a UV coating, in particular a UV paint coating, or of UV printing dyes, on a substrate, in particular on heat-sensitive materials, with at least one light source that is located above the substrate, where the light of said light source can be directed to the UV coating via a reflector system for purposes of curing, where at least one barrier prevents, at least partially, the direct beam path of the light source from striking the substrate, characterized in that the UV radiation emitted by the light source is reflected by a UV reflection coating, which is directly applied to the light source, through the light source to the reflectors located behind the light source, and the barrier includes at least one heat absorbing body that absorbs, at least partially, the heat radiation emitted by the light source.

The device subject to the invention causes an effective separation of the UV radiation from the IR radiation by making it possible to absorb more than 90% of the IR radiation. Due to the minimized path length of the radiation, the UV intensity is comparable with that of conventional devices, such as the ones according to DE 39 02 643 C2, where the light source is located directly above the irradiation goods. Furthermore, the separation of the UV and the IR radiation allows for the employment of light sources with up to eight times the energy when compared to the light sources used thus far, without increasing the heat load of the substrate. In this manner, it is possible to achieve extremely short cycle times or high throughput speeds in the production lines.

By a special geometry of the barrier with shaping for the UV reflection coating and its location directly under the light source, the reflection of the UV radiation is realized through the light source instead of directing the radiation past the lamp as was common thus far. The UV reflection coating with a semi-circular cross-section located in the shape design partially surrounds the light source at its bottom side. At least 50% of the UV radiation that strikes the UV reflection coating is reflected through the light source onto the reflectors located behind the light source due to the shape and arrangement subject to the invention.

If the UV reflection coating is applied directly at the outer side of the light source according to the aforementioned second exemplary embodiment, the UV radiation is almost entirely reflected through the light source. The losses when the UV radiation passes through the glass body of the light source and the gas are relatively low. The path of the UV radiation is minimal. Since this solution does not require special shape designs for the reflection coating at the barrier in order to reflect the UV radiation through the light source, the barrier can be designed as a geometrically simple heat absorbing body, for example, as a plate.

The heat absorbing body of the barrier together with the UV reflection coating avoids the direct heat radiation path onto the substrate.

If UV paint is used where low-molecular components evaporate, the emission of these components is reduced because of the low heat development on the substrate.

An effective separation of the UV and the IR radiation is possible if the UV reflection coating at the barrier is part of a cold light mirror. The reflectors behind the light source, which are preferably designed as cold light mirrors as well, divert only the UV radiation that is required for curing at least in part past the barrier to the substrate.

In an advantageous embodiment of the invention, boreholes are provided in the barrier, through which cooling media and/or gases can be transferred. Cooling prevents the barrier from emitting or reflecting heat radiation. The absorbed heat radiation can be transferred to the cooling medium, but also to a cooling air stream if the heat absorbing body of the barrier is equipped with cooling fins that transfer the heat to a cooling air stream. Through cooling, the heat-absorbing body of the barrier can be kept at a constant temperature by regulating the amount of heat removed.

Using the boreholes, gases such as nitrogen can be transferred as well in order to sweep the substrate. In this manner, short curing times with optimal curing can be achieved. It is particularly advantageous to deploy the gas through wide boreholes in the shape of nozzles in the barrier directly above the substrate. However, gases cannot only be deployed using these additional boreholes but alternatively also suctioned off, for example, in order to prevent low-molecular materials emitted by coatings of lower quality to deposit on the reflectors.

To focus the UV radiation in one point, the reflectors that are positioned behind the light source are, at least partially, designed cylindrically with a semi-circular cross-section. The semi-circular cross-section of the reflectors focuses the radiation in one focal point on the substrate. However, if the aim is to achieve a two-dimensional illumination, it is useful to design the reflectors behind the light source, at least partially, in plate-shape.

Providing an asymmetric arrangement of the barrier and of the reflectors, behind the light source and disposed asymmetric to a vertical plane containing the longitudinal axis of the light source and being positioned perpendicular to the surface of the substrate, has the effect that the substrate initially pre-cures when running under the device and then is irradiated with high UV intensity. Such pre-curing results in a matte finish of the UV paint coating.

The intensity of the UV radiation can be varied by making the distance between the barrier and the light source adjustable, whereby the intensity decreases as the distance increases.

A small portion of heat radiation may be required to achieve optimal curing. The portion of the radiation that gets past the barrier system can be adjusted by using an aperture system to create an adjustable barrier geometry wherein the barrier includes an aperture system with height-adjustable apertures that allows for an adjustment of the radiation that will strike the UV coating of the substrate coming from the light source without being reflected. Heat apertures that can slide fully to the barrier and are located above the substrate, wherein the barriers are capable of fully shielding the substrate from the radiation of the light source also enable an adjustment of the radiation that strikes the substrate. They can also fully prevent radiation (shutter) and thus protect the substrate from too much UV radiation when the production line is at a standstill.

Adjustment capabilities of the apertures of the aperture system, for example, may be adjustable asymmetric to a vertical plane containing the longitudinal axis of the light source and being positioned perpendicular to the surface of the substrate and/or may be adjustable from the outside during the operation of the device. Such adjustments allow for an adaptation of the heat radiation affecting the substrate to changing production conditions (environmental temperature, air humidity, process speed, etc.) while the production is running.

The adjustment system may include, for example, a electrical or pneumatic drive.

A deflection of the lamp body is prevented because of the existence of at least partial contact between the light source and the barrier, especially through support structures. This allows for the employment of lamp bodies with lengths of up to 4 m, such as those that are necessary for paint curing on very wide packaging foils or of floor coverings, for example.

Additional details and advantageous developments of the invention will become more readily apparent from the description of exemplary embodiments that in no way are to be understood as limitations of the invention with reference being made to the accompanying drawings.

BRIEF DESCRIPTION OF THE DRAWINGS

The invention will now be described by way of the drawings, in which.

DETAILED DESCRIPTION OF THE PREFERRED EMBODIMENT

Figure 1:
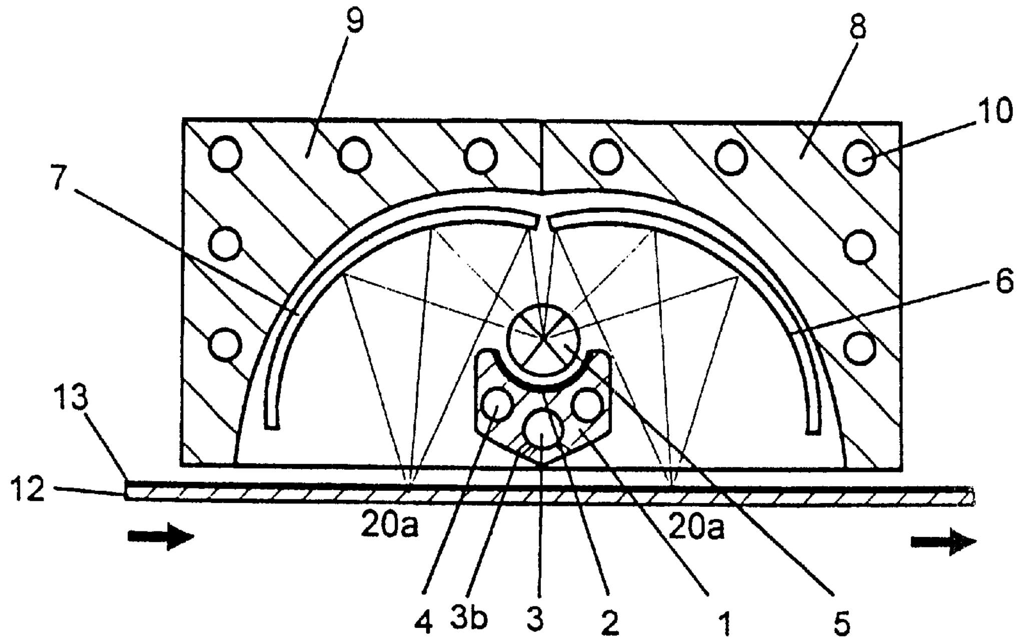
FIG. 1 is a schematic representation of a front view of a preferred exemplary embodiment of a device subject to the invention.
Figure 7:
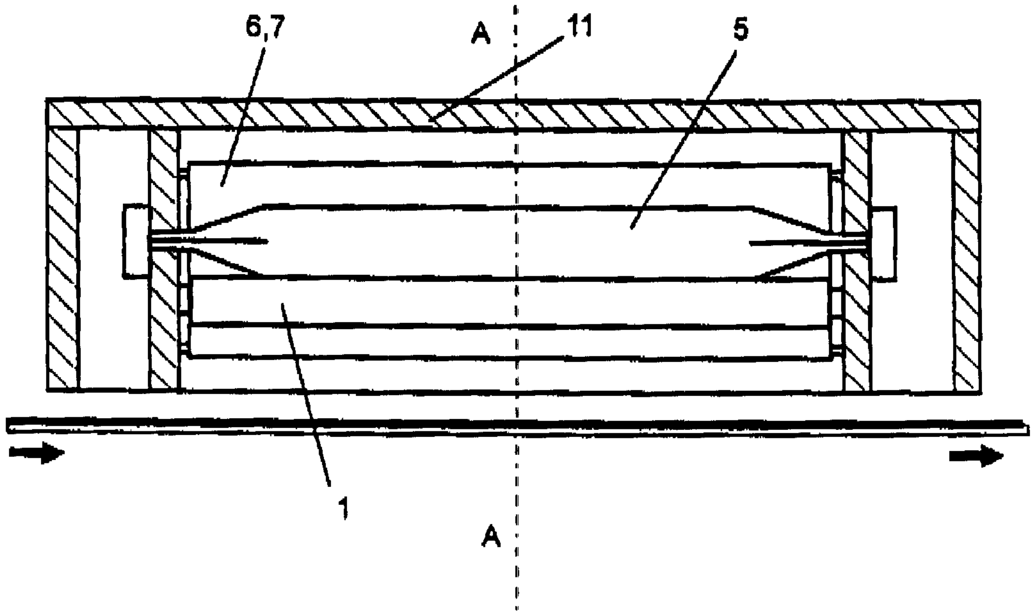
FIG. 7 is a schematic representation of a side view of a device according to FIG. 1.

FIG. 1 is a schematic presentation of a device subject to the present invention in a section A—A according to FIG. 7. FIG. 7 shows a side view of this device. A barrier consists of a heat-absorbing body (1), a UV reflection coating (2) and boreholes (3,4), which can be used for transferring cooling media or gases. Borehole (3) is provided with nozzles (3*b*) that allow for gases to be deployed directly above a substrate (12) with a UV paint coating (13) or suctioned from this location. A rod-shaped (cylindrical) light source (5) is located above the barrier. The cylindrical reflectors (6) and (7) that are arranged behind the light source (5) have a semi-circular cross-section, which makes it possible to focus the UV radiation in the two points (20*a*) on the substrate (12). The reflectors (6,7) are preferably designed as cold light mirrors to ensure an effective separation of the UV and the IR radiation. Heat absorbers (8,9) that are provided with cooling channels (10) are placed behind the reflectors (6,7) to absorb the IR radiation that is transmitted through the reflectors. It is also possible to cool the heat absorbers (8,9) with a stream of air.

Figure 2:
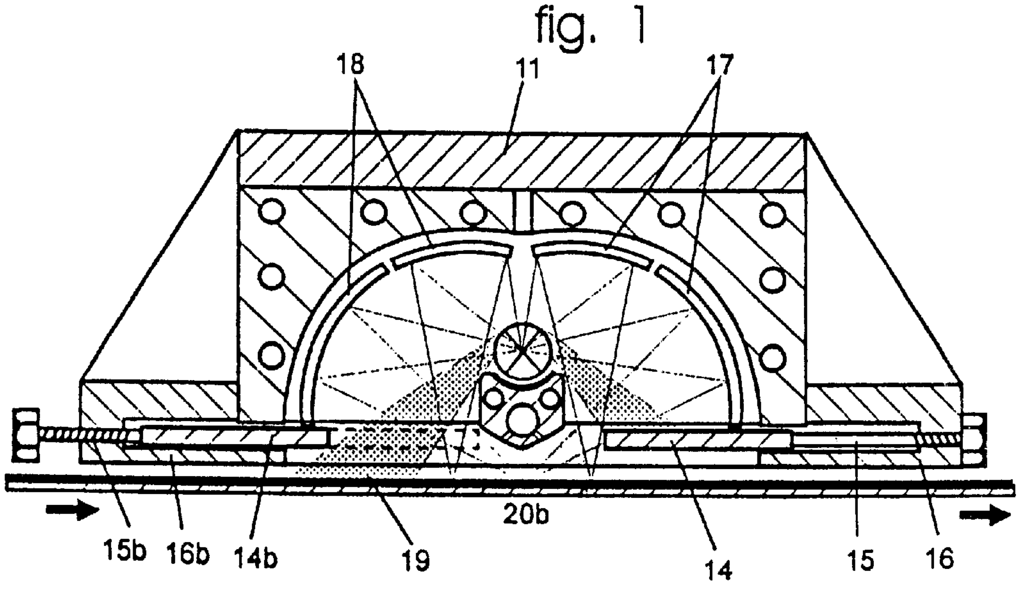
FIG. 2 is a schematic representation of a front view of a second preferred exemplary embodiment of a device subject to the invention.

FIG. 2 shows a variation of the device with heat apertures (14, 14*b*) and 3 focal points (20*b*) of the UV radiation. In similar fashion, it includes a barrier, a light source and heat absorbers. In contrast to the embodiment shown in FIG. 1, the reflectors (17,18) are comprised of two cylindrical components with semi-circular cross-sections. In this manner, the UV radiation is focused in the three points (20*b*). The heat apertures (14,14*b*) allow for a partial obstruction of the heat radiation (19). To this end, the heat apertures (14,14*b*) are closed using adjustment devices (15, 16,15*b*,16*b*) to the point where the heat radiation (19) no longer strikes the UV paint coating (13) of the substrate (12) or only strikes it partially. When the production line is stopped, it is possible to shield the coated substrate (12,13) from the radiation. By sliding the heat apertures (14,14*b*) forward to the barrier, the beam path to the substrate is fully closed (cf. position of the heat aperture (14*b*) shown as a dash line (shutter function)).

Figure 3:
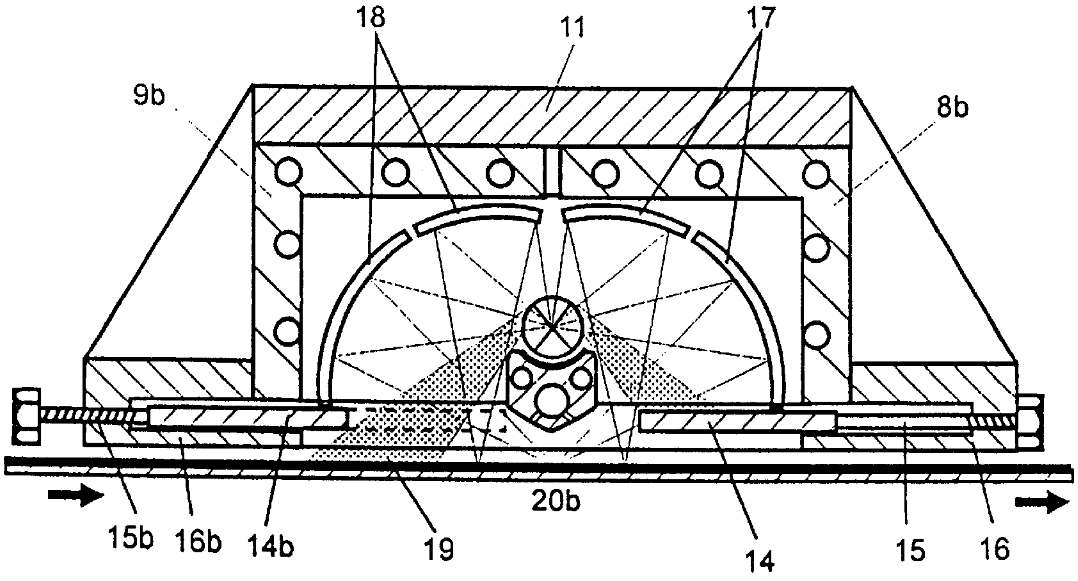
FIG. 3 is a schematic representation of a front view of a third preferred exemplary embodiment of a device subject to the invention.

FIG. 3 shows a similar device as FIG. 2. However, here the heat absorbers (8*b*,9*b*) are designed in plate-shape.

Figure 4:
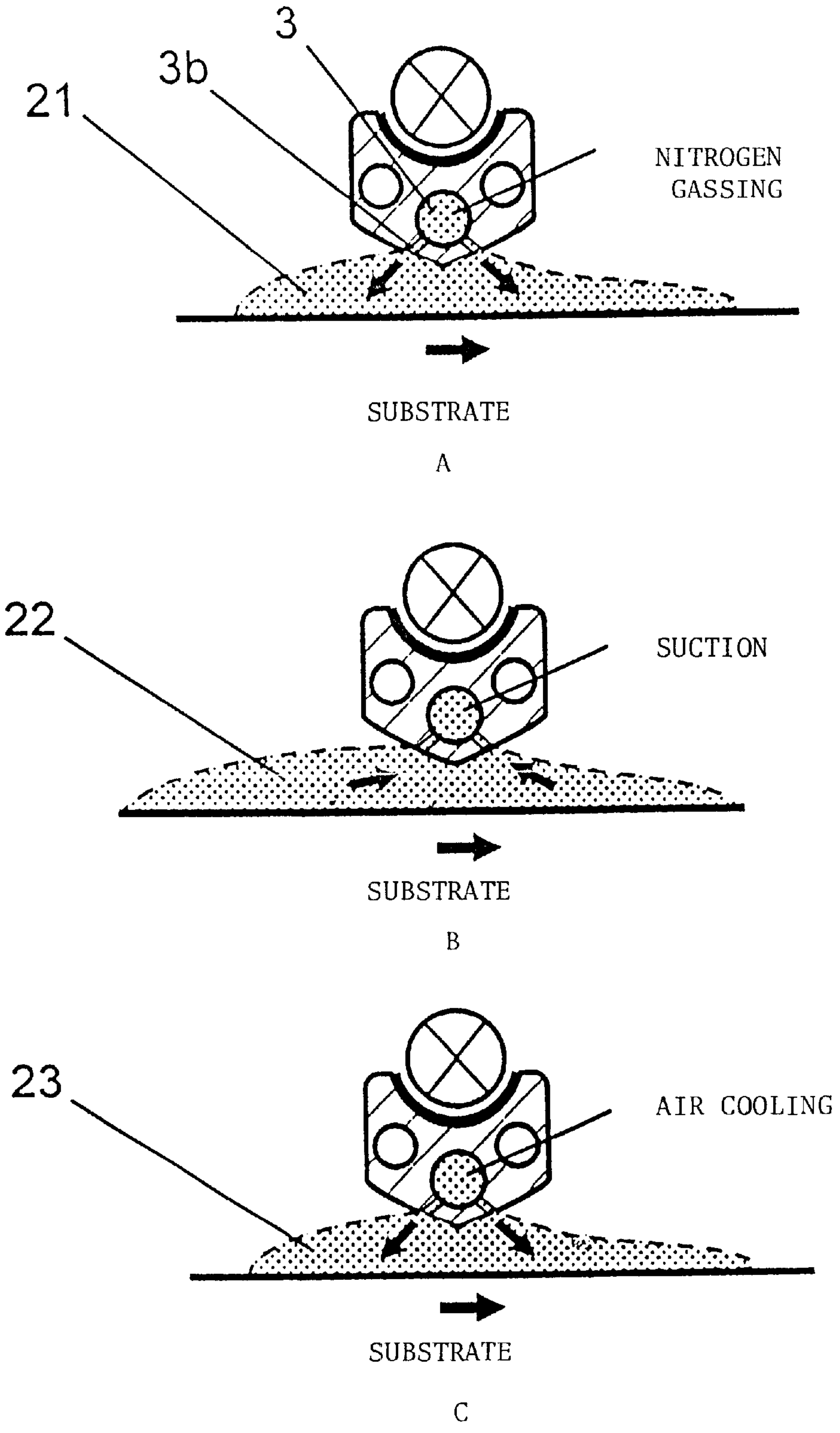
FIGS. 4A–4C are schematic representations of the functionality of gas suction and supply boreholes in barriers.

FIGS. 4A–4C clarify the functionality of the boreholes in the barrier. According to FIG. 4A, nitrogen (21) or a comparable gas can be directed to the coated substrate (12,13) through the boreholes (3) and the nozzles (3*b*). The exclusion of oxygen allows for faster and better curing of the UV paint coating (13) on the substrate (12).

If one does without the gas application, then the boreholes can be used as suction devices as shown in FIG. 4B. During normal operation, the low-molecular components given off by the UV paint coating (13) cause a quick contamination of the reflectors (6,7,17,18). To avoid this, a suction device (not shown) can be connected to the channel (3). The rising gas (22) can be suctioned off through the nozzles (3*b*).

With particularly heat-sensitive substrates, the borehole (3) can be used to transfer cooling air that cools the coated substrate (12,13) with a light air stream, as shown in FIG. 4C. At the same time, the cooling air stream (23) prevents the low-molecular substances from rising up by pushing these substances from the irradiation device.

FIGS. 5A–5E show various embodiments of the barrier. Basically, the barrier consists of an UV reflection coating (2) and a heat-absorbing body (1) unless the UV-reflection coating (2) is applied to the light source (5).

Figure 5:
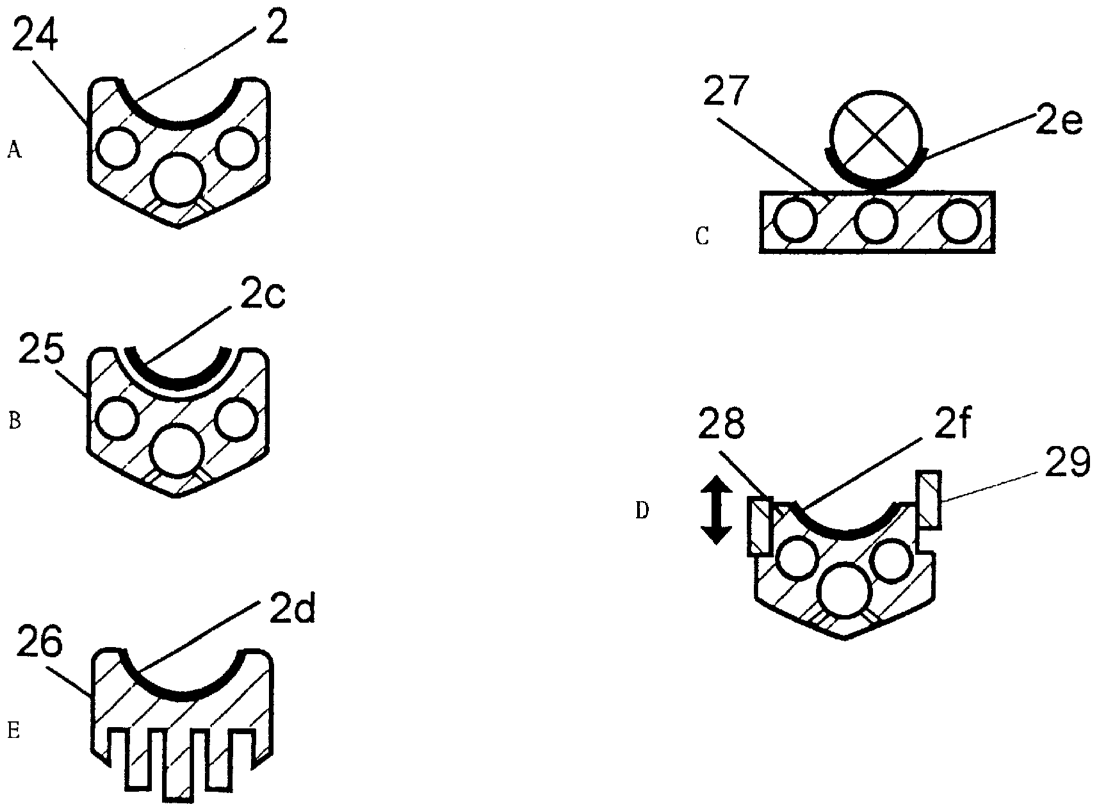
FIGS. 5A–5E show various exemplary embodiments of barriers.

The UV reflection coating (2) reflects primarily the short-wave UV radiation while it is essentially transmissive to the infrared radiation. With cold light mirrors (2*c*), as shown in FIG. 5B, the UV reflection coating is applied to glass. The cold light mirror (2*c*) is attached to the heat-absorbing body (25). The UV reflection coating (2*e*), as shown in FIG. 5C, can also be applied directly on the light source (5), for example, with the glass body serving as the carrier material for the UV reflection coating (2*e*). Furthermore, the UV reflection coating (2,2*f*,2*d*), as shown in FIGS. 5A, 5D, and 5E, can also be applied directly on the heat-absorbing body (24,26,28) of the barrier, which in this case can be made, for example, of an aluminum profile an infrared absorption coating in the shape design to prevent a backflow of the IR radiation from the aluminum profile.

The heat-absorbing bodies (24,25,27,28) of the barriers may be provided with a liquid cooling system, as shown in FIGS. 5A–5D, or the heat-absorbing body (26) may be provided with an air cooling system as shown in FIG. 5E. The geometry of the barrier is dependent on its distance to the tight source (5) and on the arrangement of the UV reflection coating (2). If the UV reflection coating (2*e*) is applied directly to the light source (5), as shown in FIG. 5C, then the heat-absorbing body (27) that forms the barrier can be designed as a plate. If the reflection coating (2,2*f*,2*d*) is applied directly to the barrier, as shown in FIGS. 5A, 5D and 5E, then the heat-absorbing body (24,25,26,29) of the barrier must be shaped according to the desired reflection properties. Even when using semi-circular cold light mirrors (2*c*), as shown in FIG. 5B, it is recommended to arrange them in a respective semi-circular shape of the heat-absorbing body (25) of the barrier. Cold light mirrors (2*c*) are easier to replace than UV reflection coatings (2,2*d*,2*e*,2*f*) that are directly applied on the heat-absorbing body of the barrier or on the light source (5).

The heat absorbing body (28) includes height-adjustable apertures (29) that can be used to adjust the portion of the direct heat radiation (19) that passes the barrier and strikes the substrate (12). With fully extended apertures (29), no heat radiation strikes the substrate directly, if the heat apertures (29) are fully retracted, a portion of the heat radiation strikes the substrate. The heat apertures (29) are preferably individually adjustable.

Figure 6:
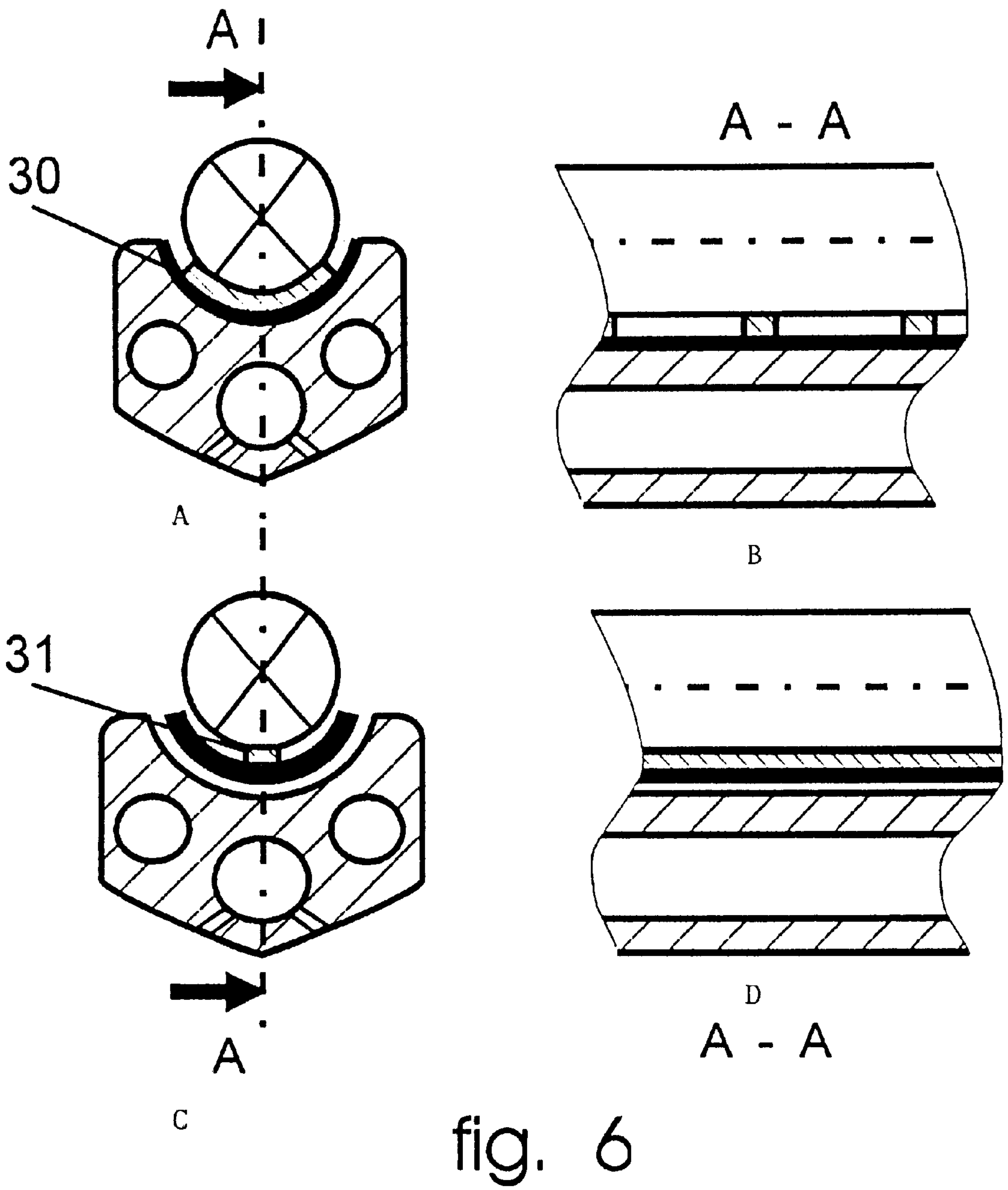
FIGS. 6A–6B and 6C–6D are schematic representations of front and side views of details of embodiments of the device according to the present invention.

FIGS. 6A and 6B show support structures (30,31) that protect the light source (5) from deflection. With particularly long light sources, their glass bodies will not be able to keep their shape at very high temperatures. The barrier together with the support structures (30,31) that establish contact between the light source and the barrier prevent the deflection. The light source rests on the support structures (30) in point-shape while it rests on the support structure (31) along the entire length. The support structures (30,31) can be located on the heat-absorbing body (1) or on the UV reflection coating (2).

Figure 8:
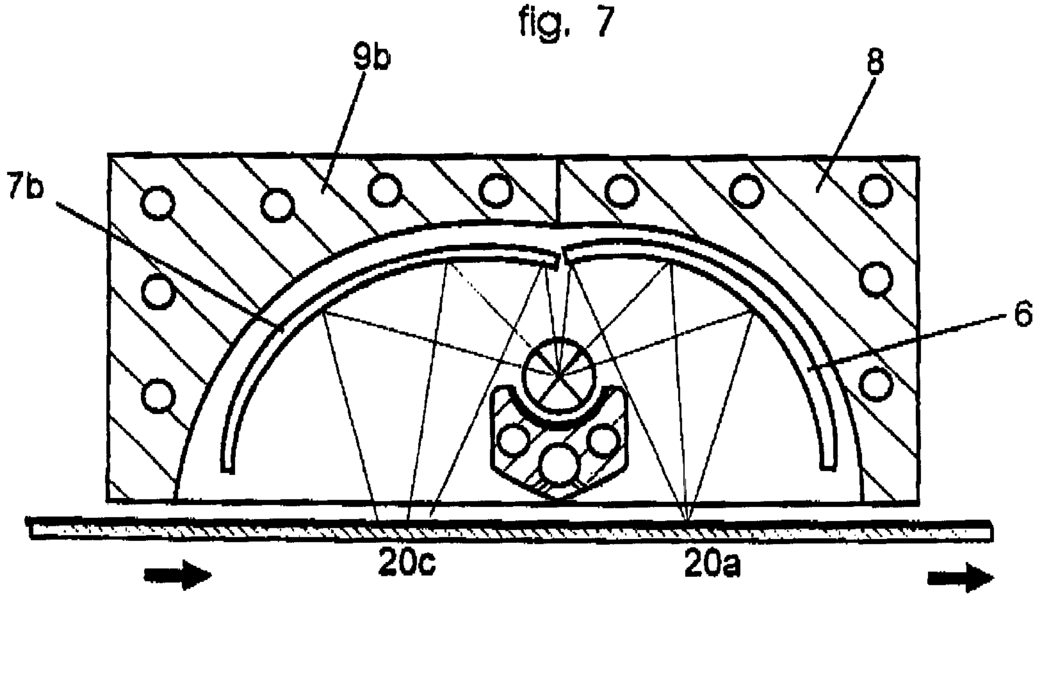
FIG. 8 is a schematic representation of a front view of a preferred exemplary embodiment of a device subject to the invention.

FIG. 8 shows a device that is built asymmetrically to a vertical plane, where the vertical plane includes the longitudinal axis of the light source (5) and is positioned perpendicular to the surface of the substrate (12). With a device of this type, the UV radiation is not focused in two points (20*a*) on the substrate as shown in FIG. 1, instead it is two-dimensionally irradiated in the area (20*c*). This area irradiation causes slight pre-curing of the UV paint coating (13), which is then completely cured in the point (20*a*). This type of curing results in a slight roughness of the UV paint coating (13) that optically looks like a matte surface. This effect is used, for example, to manufacture glare-free surfaces in instrument panels.

Although various preferred embodiments of the present invention have been described herein in detail, it will be appreciated by those skilled in the art, that variations may be made thereto without departing from the spirit of the invention or the scope of the appended claims.

What is claimed is:

1. A device for curing a UV coating (13), on a substrate (12), having at least one light source (5) for generating UV radiation that is located above the substrate (12), a reflector system (2,6,7,17,18) provided to direct the light of said light source to the UV coating (13), and at least one barrier to at least partially prevent the direct beam path of the light source from striking the substrate (12), the improvement comprising:

a UV reflection coating (2,2*d*,2*f*) disposed in a light path between the light source and the barrier to reflect the UV radiation emitted by the light source through the light source to the reflectors (6,7,17,18) located behind the light source;

at least one heat absorbing body (1,24,25,26,28) associated with the barrier that absorbs, at least partially, the heat radiation emitted by the light source.

2. The device according to claim 1, wherein the barrier disposed between the light source and substrate and provides a configured support for the UV reflection coating.

3. The device according to claim 1, wherein the UV reflection coating (2,2*d*,2*f*) is applied directly to the light source.

4. The device according to claim 1, wherein said barrier comprises at least one borehole (3,3*b*,4) adapted for transferring cooling media and/or gases.

5. The device according to claim 1, wherein the UV reflection coating (2) is part of a cold light mirror (2*c*).

6. The device as set forth in claim 1, wherein the heat absorbing body (26) of the barrier is equipped with cooling fins that transfer the heat to a cooling air stream.

7. The device according to claim 1, wherein the reflectors (6,7,17,18) behind the light source (5) are configured to deflect the UV radiation at least partially past the barrier to the coating (13) of the substrate (12).

8. The device as set forth in claim 1, the reflectors (6,7,17,18) located behind the light source (5) are, at least partially, shaped as plates.

9. The device as set forth in claim 1, wherein the reflectors (6,7,17,18) located behind the light source (5) are, at least partially, designed cylindrically with a graduated circle cross-section.

10. The device as set forth in claim 1, wherein the barrier and the reflectors (6,7,17,18) are disposed behind the light source (5) symmetric to a vertical plane containing the longitudinal axis of the light source (5) and being positioned perpendicular to the surface of the substrate (12).

11. The device as set forth in claim 1, wherein the barrier and the reflectors (6,7*b*) are disposed behind the light source (5) asymmetric to a vertical plane containing the longitudinal axis of the light source (5) and being positioned perpendicular to the surface of the substrate (12).

12. The device according to claim 1, wherein a distance between the barrier and the light source (5) is adjustable.

13. The device according claim 1, further comprising an aperture system associated with the barrier having at least one height-adjustable aperture (29) that allows for an adjustment of an unreflected portion of the radiation from the light source (5) striking the UV coating (13) of the substrate (12).

14. The device according to claim 1, further comprising at least one adjustable heat aperture (14,14*b*) located above the substrate (12), adapted to slide fully to the barrier and being capable of fully shielding the substrate (12) from the radiation of the light source (5).

15. The device according to claim 1, further comprising a set of at least two apertures (29, 14,14*b*) for adjusting a radiation reaching the substrate, said at least two apertures being adjustable asymmetrically to a vertical plane containing the longitudinal axis of the light source (5) and being positioned perpendicular to the surface of the substrate (12).

16. The device according to claim 1, further comprising at least one aperture (29,14,14*b*) for adjusting a radiation reaching the substrate, said aperture being externally adjustable during the operation of the device.

17. The device according to claim 1, further comprising at least one aperture (29,14,14*b*) for adjusting a radiation reaching the substrate, said aperture being adjustable using an electric or pneumatic drive.

18. The device according to claim 1, wherein the radiation reflected by the UV reflection coating (2) through the light source (5) is, at least partially, focussed by the reflectors (6,7,17,18) on the coating (13) of the substrate (12).

19. The device according to claim 1, further comprising a contact between the barrier and the light source (5).

20. The device according to claim 1, further comprising at least one support structure (30,31) provided in a gap between the barrier and the light source (5) that prevents a deflection of a body of the light source (5).

21. The device according to claim 1, wherein said device has at least a portion of an exit aperture thereof which transmits substantially only UV light which has been reflected at least once toward the UV coating.

22. The device according to claim 1, further comprising a controllable barrier, wherein the controllable barrier selectively controls an amount of heat radiation irradiating the UV coating.

23. The device according to claim 1, wherein at least 50% of the UV radiation is reflected through the light source onto the reflector system.

24. The device according to claim 1, wherein said UV reflection coating is concave with respect to the light source.

25. A device for optically curing a coating, on a heat-sensitive substrate, comprising:

a light source, adapted for generating optical and heat radiation, in proximity to the substrate;

a barrier, disposed along a direct path between the light source and the heat-sensitive substrate, having associated therewith a heat radiation absorbing portion;

a selective optical radiation reflector, disposed along an indirect path between the light source and substrate, for reflecting optical radiation from and through the light source toward the substrate: and a distinct selective optical radiation reflective surface, disposed between the light source and the barrier, for reflecting optical radiation from the light source back through the light source toward the optical radiation reflector, wherein optical and heat radiation generated by the light source is propagated along a first path to the optical radiation reflective surface, wherein optical radiation is selectively reflected back through the light source, to the selective optical radiation reflector and to the substrate, and heat radiation is at least partially absorbed by the heat radiation absorbing portion, and along a second path from the light source to the selective optical radiation reflector, wherein optical radiation is selectively reflected to the substrate, and at least a portion of the heat radiation is not reflected, whereby a ratio of optical radiation to heat radiation is respectively increased between the light source and substrate.

26. The device according to claim 25, wherein the selective optical radiation reflective surface is integrated with the light source.

27. The device according to claim 25, wherein the selective optical radiation reflective surface is supported by the barrier to selectively reflect the optical radiation back through the light source.

28. The device according to claim 25, wherein said device has at least a portion of an exit aperture thereof which transmits substantially only optical radiation which has been reflected at least once.

29. The device according to claim 25, further comprising a controllable barrier, wherein the controllable barrier selectively controls a ratio of optical radiation to heat radiation directed toward the substrate.

30. The device according to claim 25, wherein at least 50% of the optical radiation is reflected through the light source onto the selective optical radiation reflector.

31. The device according to claim 25, wherein said a selective optical radiation reflective surface is concave with respect to the light source.

32. A method for optically curing a coating, on a heat-sensitive substrate, comprising the steps of:

providing a light source, adapted for generating optical and heat radiation, in proximity to the substrate;

disposing a barrier along a direct path between the light source and the heat-sensitive substrate, having associated therewith a heat radiation absorbing portion;

selectively reflecting optical radiation from and through the light source toward the substrate, with a selective optical radiation reflector, disposed along an indirect path between the light source and substrate: and selectively reflecting optical radiation from the light source back through the light source toward the optical radiation reflector, with a distinct selective optical radiation reflective surface, disposed between the light source and the barrier, wherein optical and heat radiation generated by the light source is propagated along a first path to the optical radiation reflective surface, wherein optical radiation is selectively reflected back through the light source, to the selective optical radiation reflector and to the substrate, and heat radiation is at least partially absorbed by the heat radiation absorbing portion, and along a second path from the light source to the selective optical radiation reflector, wherein optical radiation is selectively reflected to the substrate, and at least a portion of the heat radiation is not reflected, whereby a ratio of optical radiation to heat radiation is respectively increased between the light source and substrate.

33. The method according to claim 32, further comprising the step of transmitting through at least a portion of an exit aperture substantially only optical radiation which has been reflected at least once.

34. The method according to claim 32, further comprising the step of selectively controlling a ratio of optical radiation to heat radiation directed toward the substrate.

35. The device method to claim 32, wherein said step of selectively reflecting optical radiation from the light source back through the light source toward the optical radiation reflector, with a selective optical radiation reflective surface, comprises reflecting at least 50% of the optical radiation through the light source onto the selective optical radiation reflector.

36. The method according to claim 32, further comprising the step of convergingly reflecting the optical radiation from the selective optical radiation reflective surface.

* * * * *